(12) United States Patent
Wu et al.

(10) Patent No.: US 7,947,960 B2
(45) Date of Patent: May 24, 2011

(54) DETECTOR PANEL AND X-RAY IMAGING APPARATUS (75) Inventors: Zhu Wu, Beijing (CN); Michael J. Utschig, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 98 days.

(21) Appl. No.: 12/358,836

(22) Filed: Jan. 23, 2009

(65) Prior Publication Data

US 2009/0202044 A1 Aug. 13, 2009

(30) Foreign Application Priority Data

Feb. 13, 2008 (CN) .......................... 2008 1 0074218

(51) Int. Cl.
*G01T 1/00* (2006.01)
(52) U.S. Cl. .................................................. 250/370.09
(58) Field of Classification Search ............. 250/370.09, 250/370.01, 370.08; 378/4, 19
See application file for complete search history.

(56) References Cited

U.S. PATENT DOCUMENTS

| | | | |
|---|---|---|---|
| 4,681,227 A | 7/1987 | Tamura et al. | |
| 4,922,105 A | 5/1990 | Hosoi | |
| 5,081,543 A | 1/1992 | Romandi | |
| 5,514,873 A | 5/1996 | Schulze-Ganzlin et al. | |
| 5,804,832 A | 9/1998 | Crowell et al. | |
| 5,877,501 A | 3/1999 | Ivan et al. | |
| 5,912,941 A | 6/1999 | Schmitt | |
| 6,091,982 A | 7/2000 | Reinke et al. | |
| 6,205,119 B1 | 3/2001 | Kaczynski | |
| 6,575,624 B2 | 6/2003 | Noegel et al. | |
| 6,700,126 B2 | 3/2004 | Watanabe | |
| 6,825,472 B2 * | 11/2004 | Endo | 250/370.09 |
| 7,016,467 B2 | 3/2006 | Brooks | |
| 7,057,181 B2 | 6/2006 | Yagi | |
| 7,078,703 B2 | 7/2006 | Watanabe | |
| 7,164,137 B2 | 1/2007 | Hayashida | |
| 7,189,972 B2 | 3/2007 | Ertel et al. | |
| 7,202,481 B2 * | 4/2007 | Spahn et al. | 250/370.09 |
| 7,317,190 B2 | 1/2008 | Ertel et al. | |
| 7,342,998 B2 | 3/2008 | Kump et al. | |
| 7,396,159 B2 | 7/2008 | Utschig et al. | |
| 7,429,737 B2 | 9/2008 | Wojcik et al. | |
| 7,435,967 B2 | 10/2008 | Ertel et al. | |
| 7,488,946 B2 | 2/2009 | Hennessy et al. | |
| 7,495,226 B2 | 2/2009 | Jadrich et al. | |
| 7,581,883 B2 | 9/2009 | Kato | |
| 2002/0150214 A1 | 10/2002 | Spahn | |

FOREIGN PATENT DOCUMENTS

JP 2002-336227 11/2002

* cited by examiner

*Primary Examiner* — David P Porta
*Assistant Examiner* — Mark R Gaworecki
(74) *Attorney, Agent, or Firm* — Armstrong Teasdale LLP (57) ABSTRACT

A portable detector panel includes an X-ray detector assembly having an X-ray detecting surface on its surface, a box-like case that houses the X-ray detector assembly therein and whose upper part that is opposite to the X-ray detecting surface is X-ray transmissive, and a spacer that supports the X-ray detector assembly housed in the case so as to be apart from the inner bottom wall of the case, wherein the spacer is arranged between the X-ray detector assembly and the inner bottom wall of the case, is made of a hard material, and has a flexible shape with respect to the movement of the X-ray detector assembly in the direction substantially parallel to the X-ray detecting surface.

20 Claims, 10 Drawing Sheets

DETECTOR PANEL AND X-RAY IMAGING APPARATUS

CROSS REFERENCE TO RELATED APPLICATIONS

This application claims the benefit of Chinese Patent Application No. 200810074218.6 filed Feb. 13, 2008, which is hereby incorporated by reference in its entirety.

BACKGROUND OF THE INVENTION

The embodiments described herein relate to a detector panel and an X-ray imaging apparatus, and more particularly to a portable detector panel having an X-ray detector assembly housed in a case, and an X-ray imaging apparatus using such detector panel.

As a type of X-ray imaging apparatuses, there are mobile imaging apparatuses. The X-ray imaging apparatus of this type is composed of a movable system console and a portable detector panel. The system console includes an X-ray irradiator and a control circuit, while the detector panel is composed of an X-ray detector assembly and an X-ray transmissive flat case.

The X-ray imaging apparatus is carried to a hospital room of a patient for carrying out radiography. The radiography is carried out in the hospital room in such a manner that the detector panel is put on a part of the patient to be imaged, and an X-ray is irradiated from the opposite side. The X-ray signal detected by the detector panel is transmitted to the system console with wire or wirelessly (see, for example, Japanese Unexamined Patent Publication No. 2002-336227 (paragraph numbers 0017 to 0020, FIG. 1)).

The X-ray detector assembly includes an X-ray detector including a two-dimensional array of X-ray detecting elements that convert the incident X-ray into an electrical signal, a support substrate, an interface circuit, and a flexible circuit board that connects the X-ray detector and the interface circuit.

The two-dimensional array of the X-ray detecting elements is mounted to the surface of the support substrate, the interface circuit is mounted to the back surface of the support substrate, and the flexible circuit is mounted from the surface of the support substrate to the back surface.

The X-ray detector described above is rigidly fixed to the inner bottom wall of the case via a spacer made of an appropriate hard material, or fixed through a cushion that is made of a soft material and arranged below the spacer for absorbing impact (see, for example, U.S. Pat. No. 6,700,126 (columns 3 to 5, FIG. 4)).

BRIEF DESCRIPTION OF THE INVENTION

When the X-ray detector assembly is fixed in the case through the spacer made of a hard material, a shock produced when the detector panel is dropped on the floor and hit against something is directly transmitted, so that the X-ray detector assembly is susceptible to breakdown. When the cushion is arranged below the spacer, the shock to the X-ray detector assembly is eased, but there is a problem in the reliability of the cushion material.

Since the cushion is interposed, the precise positioning of the X-ray detector assembly becomes difficult, which brings poor productivity. Further, the stability of the X-ray detector assembly to the external environment is poor due to the temperature characteristic of the cushion or the affect by the external vibration.

In view of this, a detector panel is provided having shock resistance and excellent stability to the external environment, and an X-ray imaging apparatus that uses the detector panel.

In a first aspect, a portable detector panel includes an X-ray detector assembly having an X-ray detecting surface on its surface, a box-like case that houses the X-ray detector assembly therein and whose at least upper part that is opposite to the X-ray detecting surface is X-ray transmissive, a spacer that supports the X-ray detector assembly housed in the case so as to be apart from the inner bottom wall of the case, wherein the spacer is arranged between the X-ray detector assembly and the inner bottom wall of the case, and is made of a hard material having a flexible shape with respect to the movement of the X-ray detector assembly in the direction substantially parallel to the X-ray detecting surface.

In a second aspect, the flexible shape of the spacer with respect to the movement of the X-ray detector assembly in the direction substantially parallel to the X-ray detecting surface is a cylindrical shape in which a part thereof in the height direction, which is the direction vertical to the inner bottom surface of the case, is narrower than the other part.

In a third aspect, the flexible shape of the spacer with respect to the movement of the X-ray detector assembly in the direction substantially parallel to the X-ray detecting surface is a cylindrical shape in which at least a central part is hollow.

In a fourth aspect, the X-ray detector assembly includes a support substrate, an X-ray detector supported on the upper surface of the support substrate, an electric circuit board supported on the lower surface of the support substrate, and a flexible circuit board that electrically connects the X-ray detector with the electric circuit.

In a fifth aspect, the spacer is connected to the support substrate of the X-ray detector assembly and the inner bottom wall of the case.

In a sixth aspect, the spacers are provided at four corners of the X-ray detector assembly.

In a seventh aspect, the portable detector panel also includes a buffer member that is arranged between the inner side wall of the case and the X-ray detector assembly, is made of a hard material, and has a flexible shape with respect to the movement of the X-ray detector assembly in the direction generally parallel to the X-ray detecting surface.

In an eighth aspect, the buffer member includes a beam that is arranged on the inner side wall of the case and is flexible with respect to the pressing force to the X-ray detector assembly in the direction generally parallel to the X-ray detecting surface.

In a ninth aspect, the buffer member includes a beam that is arranged between the inner side wall of the case and the X-ray detector assembly and is flexible with respect to the pressing force to the X-ray detector assembly in the direction generally parallel to the X-ray detecting surface.

In a tenth aspect, an X-ray imaging apparatus includes a system console having an X-ray irradiator and a control circuit, and a portable detector panel that detects an X-ray generated from the X-ray irradiator, wherein the detector panel includes an X-ray detector assembly having an X-ray detecting surface on its surface, a box-like case that houses the X-ray detector assembly therein and whose at least upper part that is opposite to the X-ray detecting surface is X-ray transmissive, and a spacer that supports the X-ray detector assembly housed in the case so as to be apart from the inner bottom wall of the case, the spacer being arranged between the X-ray detector assembly and the inner bottom wall of the case, and made of a hard material having a flexible shape with respect to the movement of the X-ray detector assembly in the direction substantially parallel to the X-ray detecting surface.

In an eleventh aspect, the flexible shape of the spacer with respect to the movement of the X-ray detector assembly in the direction substantially parallel to the X-ray detecting surface is a cylindrical shape in which a part thereof in the height direction, which is the direction vertical to the inner bottom surface of the case, is narrower than the other part.

In a twelfth aspect, the flexible shape of the spacer with respect to the movement of the X-ray detector assembly in the direction substantially parallel to the X-ray detecting surface is a cylindrical shape in which at least a central part is hollow.

In a thirteenth aspect, the X-ray detector assembly includes a support substrate, an X-ray detector supported on the upper surface of the support substrate, an electric circuit board supported on the lower surface of the support substrate, and a flexible circuit board that electrically connects the X-ray detector and the electric circuit.

In a fourteenth aspect, the spacer is connected to the support substrate of the X-ray detector assembly and the inner bottom wall of the case.

In a fifteenth aspect, the spacers are provided at four corners of the X-ray detector assembly.

In a sixteenth aspect, the detector panel of the X-ray imaging apparatus also includes a buffer member that is arranged between the inner side wall of the case and the X-ray detector assembly, is made of a hard material, and has a flexible shape with respect to the movement of the X-ray detector assembly in the direction generally parallel to the X-ray detecting surface.

In a seventeenth aspect, the buffer member includes a beam that is arranged on the inner side wall of the case and is flexible with respect to the pressing force to the X-ray detector assembly in the direction generally parallel to the X-ray detecting surface.

In an eighteenth aspect, the buffer member includes a beam that is arranged between the inner side wall of the case and the X-ray detector assembly and is flexible with respect to the pressing force to the X-ray detector assembly in the direction generally parallel to the X-ray detecting surface.

Embodiments described herein provide a detector panel that includes a spacer that is arranged between the X-ray detector assembly and the inner bottom wall of the case, and is made of a hard material having a flexible shape with respect to the movement of the X-ray detector assembly in the direction substantially parallel to the X-ray detecting surface. Therefore, embodiments described herein provide a detector panel having shock resistance and excellent stability with respect to the external environment, and an X-ray imaging apparatus that uses the detector panel.

DETAILED DESCRIPTION OF THE INVENTION

Figure 1:
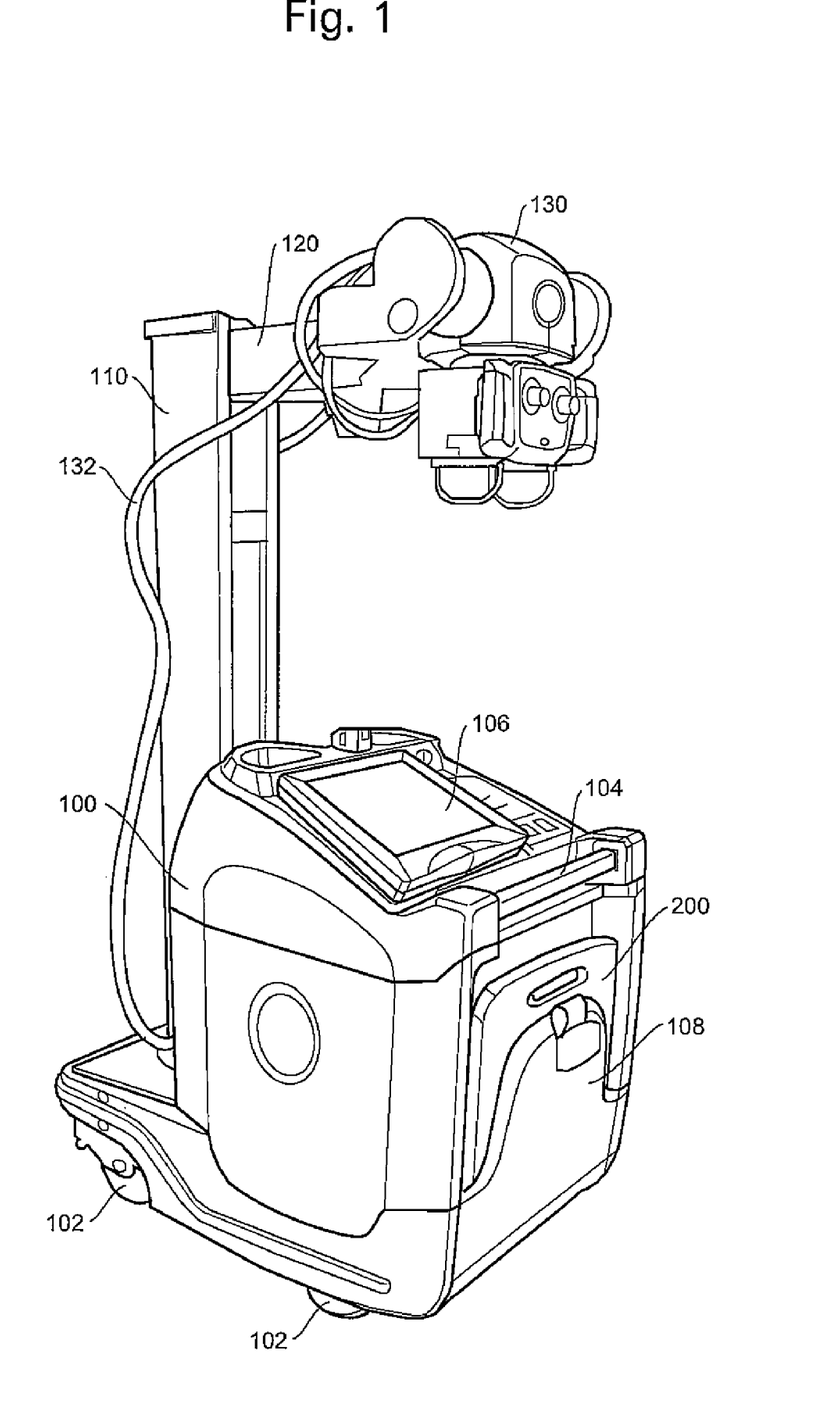
FIG. 1 is a view showing an appearance of an exemplary X-ray imaging apparatus.

Various embodiments of the present invention will be explained in detail with reference to the drawings. The present invention is not limited to the embodiments described herein. FIG. 1 schematically shows the appearance of an X-ray imaging apparatus. The configuration of this apparatus represents only one example of the X-ray imaging apparatus.

Figure 2:
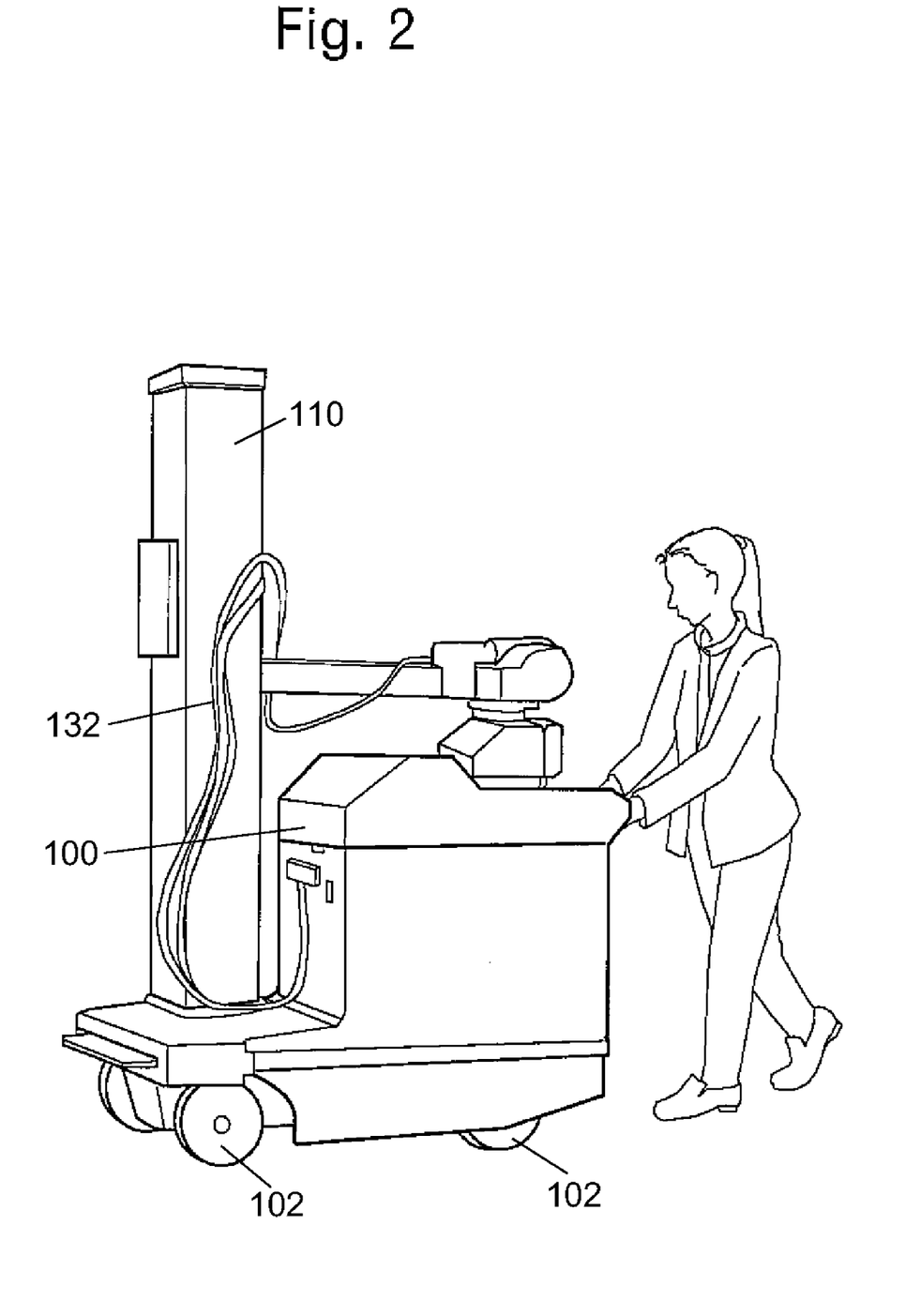
FIG. 2 is a view showing the state in which the X-ray imaging apparatus shown in FIG. 1 is being moved.

As shown in FIG. 1, the present apparatus has a system console 100. The system console 100 has a box-like structure of substantially a rectangular solid, and has an electric circuit for imaging control in its inside. The system console 100 has a caster 102 for movement at its lower part and a grip handle 104 at its upper part. Thus, the present apparatus becomes a movable X-ray imaging apparatus that can be freely moved as shown in FIG. 2.

An operation panel 106 is provided to the upper surface of the system console 100. The operation panel 106 includes a man-machine communication device such as, for example, a graphic display or a keyboard.

A vertical column 110 is provided to the back of the system console 100. An X-ray irradiator 130 is mounted to a leading end of an arm 120 that extends horizontally from the column 110. The X-ray irradiator 130 generates X-ray by a high voltage supplied from the system console 100 through a cable 132.

The direction of the X-ray irradiator 130 is changeable at the leading end of the arm 120. The arm 120 can be moved up and down along the column 110. The column 110 is spinnable about the longitudinal shaft.

The present apparatus has a detector panel 200. The detector panel 200 has a plate-like structure of substantially a rectangular shape. It is provided separate from the system console 100, and is portable. The detector panel 200 is stored in a bin 108 at the front of the system console 100 when radiography is not carried out. When the radiography is carried out, the detector panel 200 is take out of the bin 108 for use. The detector panel 200 is one example of a best mode for carrying out the present invention. The configuration of the detector panel 200 illustrates one example of the best mode for carrying out the present invention relating to a detector panel.

Figure 3:
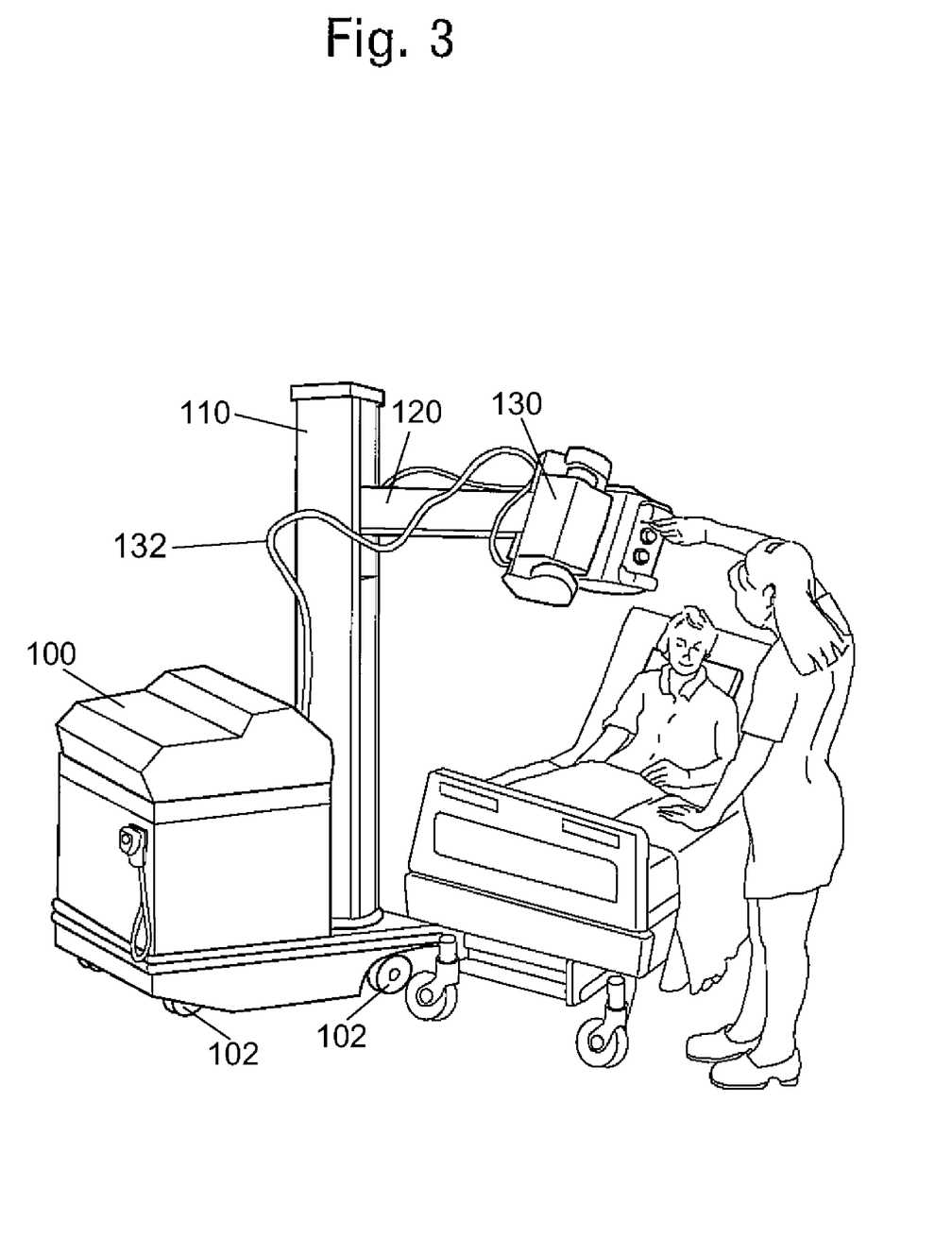
FIG. 3 is a view showing the state in which a patient is imaged by the X-ray imaging apparatus shown in FIG. 1.

FIG. 3 shows the scene when the present apparatus is used. As shown in FIG. 3, the present apparatus is used in a hospital room. Radiography is carried out in such a manner that the detector panel 200 is put on the back of a patient, and X-ray is irradiated from the front side by the X-ray irradiator 130 of the system console 100. The X-ray signal detected by the detector panel 200 is transmitted wirelessly or by a cable (not shown) to the system console 100.

Figure 4:
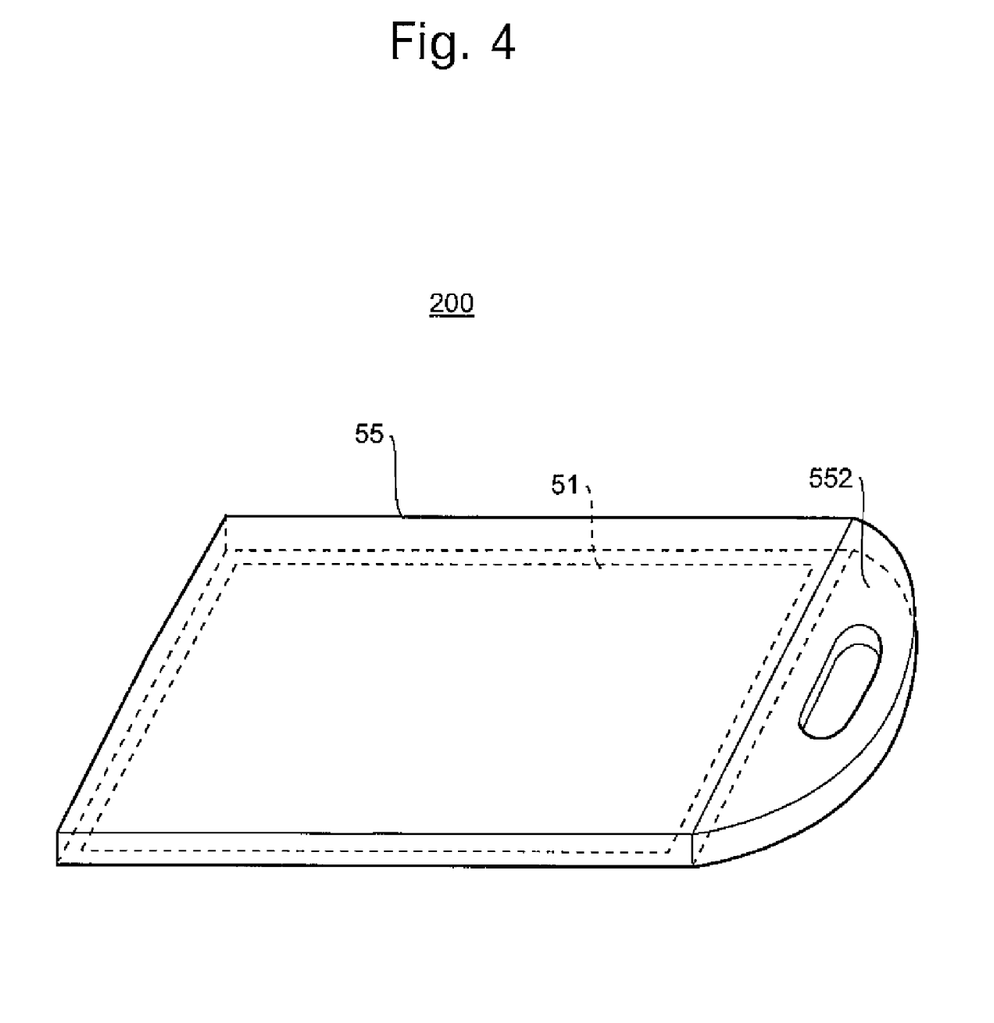
FIG. 4 is a view showing a basic configuration of an exemplary detector panel that may be used with the X-ray imaging apparatus shown in FIG. 1.

FIG. 4 shows a basic configuration of the detector panel 200. As shown in FIG. 4, the detector panel 200 has a box-like case 55 and a rectangular plate-like X-ray detector assembly 51 housed in the case 55. The upper part of the case 55 that is opposite to an X-ray detecting surface 52a' of the X-ray detector assembly 51 is made of an X-ray transmissive material. The case 55 has a grip 552 at its one end.

Figure 5:
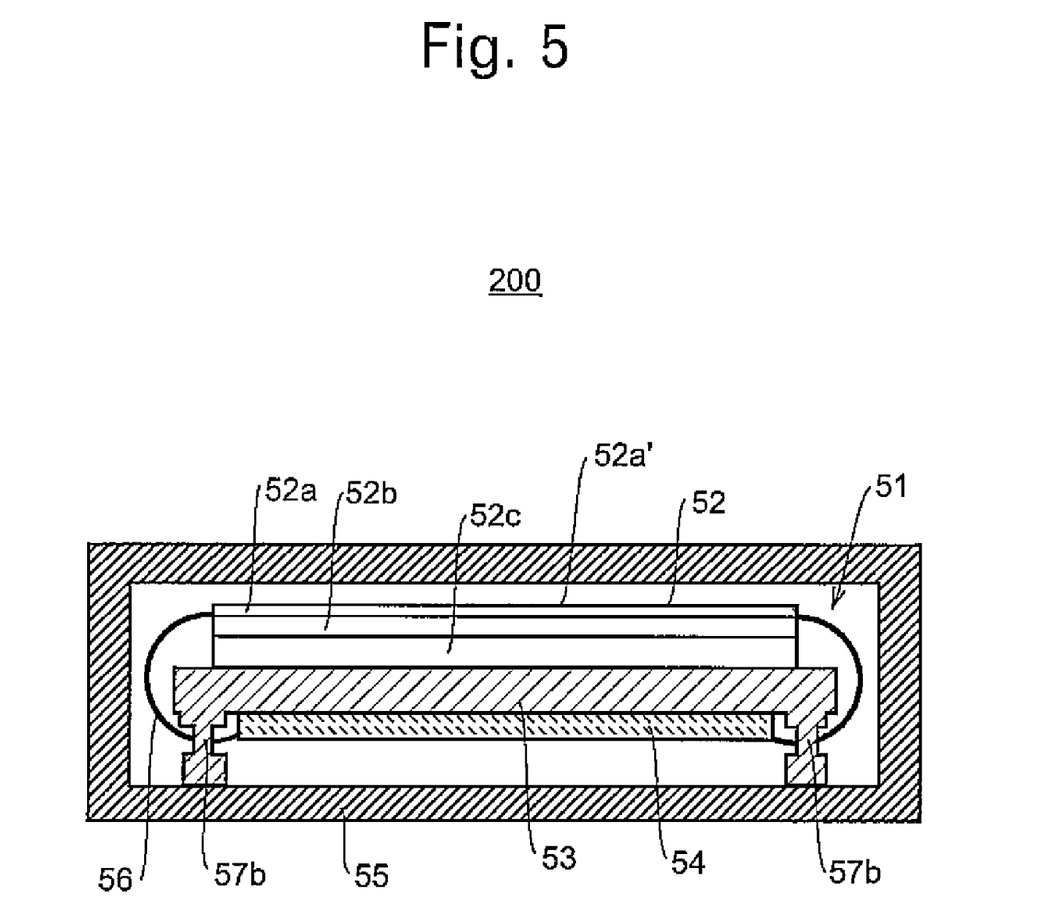
FIG. 5 is a vertical sectional view showing a basic configuration of the detector panel shown in FIG. 4.

FIG. 5 shows one example of an internal configuration of the detector panel 200. FIG. 5 is a vertical sectional view of the detector panel 200. As shown in FIG. 5, the X-ray detector assembly 51 is composed of an X-ray detector 52, a support substrate 53, and an electronic circuit board 54. The X-ray detector 52 is mounted to the surface of the support substrate 53, and the electronic circuit board 54 is mounted to the back surface of the support substrate 53, wherein both are electrically connected by a flexible circuit board 56.

The X-ray detector 52 includes a scintillator layer 52a and a photoelectric conversion layer 52b, which are laminated on a glass substrate 52c. X-ray is converted into light by the scintillator layer 52a, and the light is converted into an electric signal by the photoelectric conversion layer 52b. The photoelectric conversion layer 52b is composed of a two-dimensional array of a photoelectric conversion element such as, for example, a photo diode. The converted electric signal is inputted to the electric circuit board 54 through the flexible circuit board 56.

An electric circuit is mounted to the electric circuit board 54. The electric circuit is an interface to the system console 100. It converts the inputted signal into digital data and transmits the resultant to the system console 100 wirelessly or by a cable (not shown).

Four spacers 57b are formed at the corners of the back surface of the support substrate 53. The support substrate 53 stands on the inner bottom wall of the case 55 by the spacers 57b.

The spacers 57b are integral with the support substrate 53. The spacers 57b are formed by, for example, integrally forming with the support substrate 53. The leading ends of the spacers 57b are fixed to the inner bottom wall of the case 55 with adhesion or screw.

Each of the spacers 57b is made of a hard material, and has a cylindrical shape whose central portion in the height direction of the spacer is narrow. Therefore, the spacer 57b has a flexible shape with respect to the shock or vibration in the horizontal direction (the direction generally parallel to the X-ray detecting surface 52a') exerted to the X-ray detector assembly.

Specifically, since the spacer 57b is made of a hard material, it firmly holds the support substrate 53. Further, since the spacer 57b has a narrow cylindrical portion at its central portion, the spacer 57b has a flexible shape that bends with the movement of the support substrate 53 in the horizontal direction.

The flexible shape here means the shape that functions as a rigid body with respect to a shock or vibration produced upon a normal use, and that functions as an elastic body so as to absorb energy with respect to an extreme shock or vibration applied when dropped on a floor or hit against something. The spacer 57b described above can be realized by appropriately designing the material, shape and size.

The spacer 57b functions as a rigid support mechanism in a normal used state. Therefore, the precise positioning of the X-ray detector assembly 51 is easy, and further, the excellent and stable productivity can be provided.

On the other hand, when an extreme shock or vibration is applied in the horizontal direction, the spacer 57b functions as a buffer mechanism. It is when the corner or edge of the detector panel 200 hits against a floor or substance that the extreme shock or vibration in the horizontal direction is applied.

Since the spacer 57b functions as a buffer mechanism, the shock or the like to the X-ray detector assembly 51 is eased, whereby the X-ray detection assembly 51 is less susceptible to breakdown. Further, a cushion material or the like is not used for buffer so that reliability is enhanced.

Figure 6:
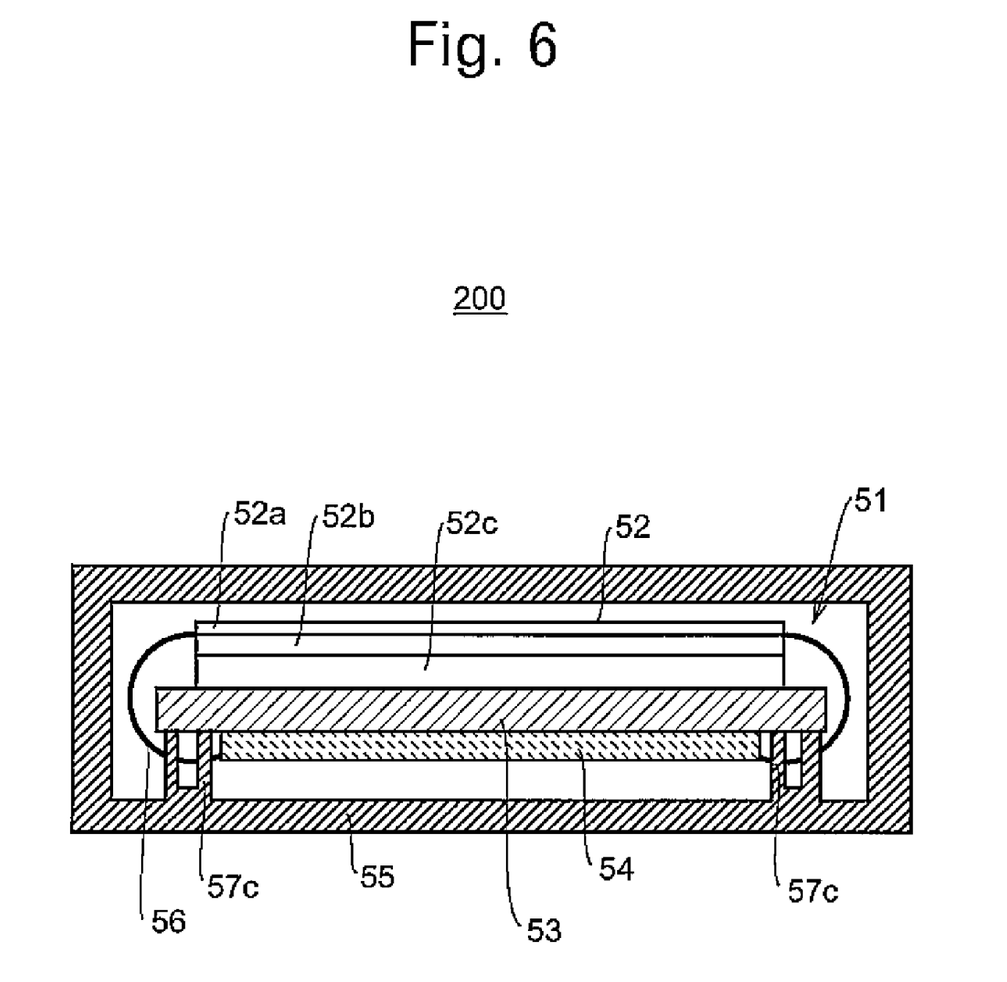
FIG. 6 is a vertical sectional view showing another basic configuration of the detector panel shown in FIG. 4.

The X-ray detector assembly 51 may be supported by spacers 57c composed of plural columns raising from the inner bottom of the case 55 as shown in FIG. 6. The spacers 57c are integral with the case 55. The spacers 57c are formed by, for example, integrally forming with the case 55. The X-ray detector assembly 51 is fixed to the leading ends of the spacers 57c with adhesion or screw.

Each of the spacers 57c is made of a hard material, and has a cylindrical shape whose central portion is narrow. Therefore, the spacer 57c has a flexible shape with respect to the shock or vibration in the horizontal direction exerted to the X-ray detector assembly 51.

Specifically, the spacer 57c has four thin columns made of a hard material arranged with a space, so that the spacer 57c firmly supports the support substrate 53. Further, the spacer 57c has a flexible shape that bends with the horizontal movement of the support substrate 53 by the thin columns. The flexible shape described above is realized by appropriately setting the material, shape and size of the spacer 57c.

The spacer 57c functions as a rigid support mechanism in a normal used state. Therefore, the precise positioning of the X-ray detector assembly 51 is easy, and further, the excellent and stable productivity is provided.

On the other hand, when an extreme shock or vibration is applied in the horizontal direction, the spacer 57c functions as a substantial buffer mechanism. Therefore, the shock or the like to the X-ray detector assembly 51 is eased, whereby the X-ray detection assembly 51 is less susceptible to breakdown. Further, a cushion material or the like is not used for buffer, so that reliability is enhanced.

It is preferable that a space to some degree is formed between the X-ray detector assembly 51 and the inner side wall of the case in order to avoid the contact therebetween when a shock is applied. Further, it is preferable that a buffer member that provides a buffer action to the horizontal movement of the X-ray detector assembly 51 is provided between the X-ray detector assembly 51 and the inner side wall of the case.

Figure 7:
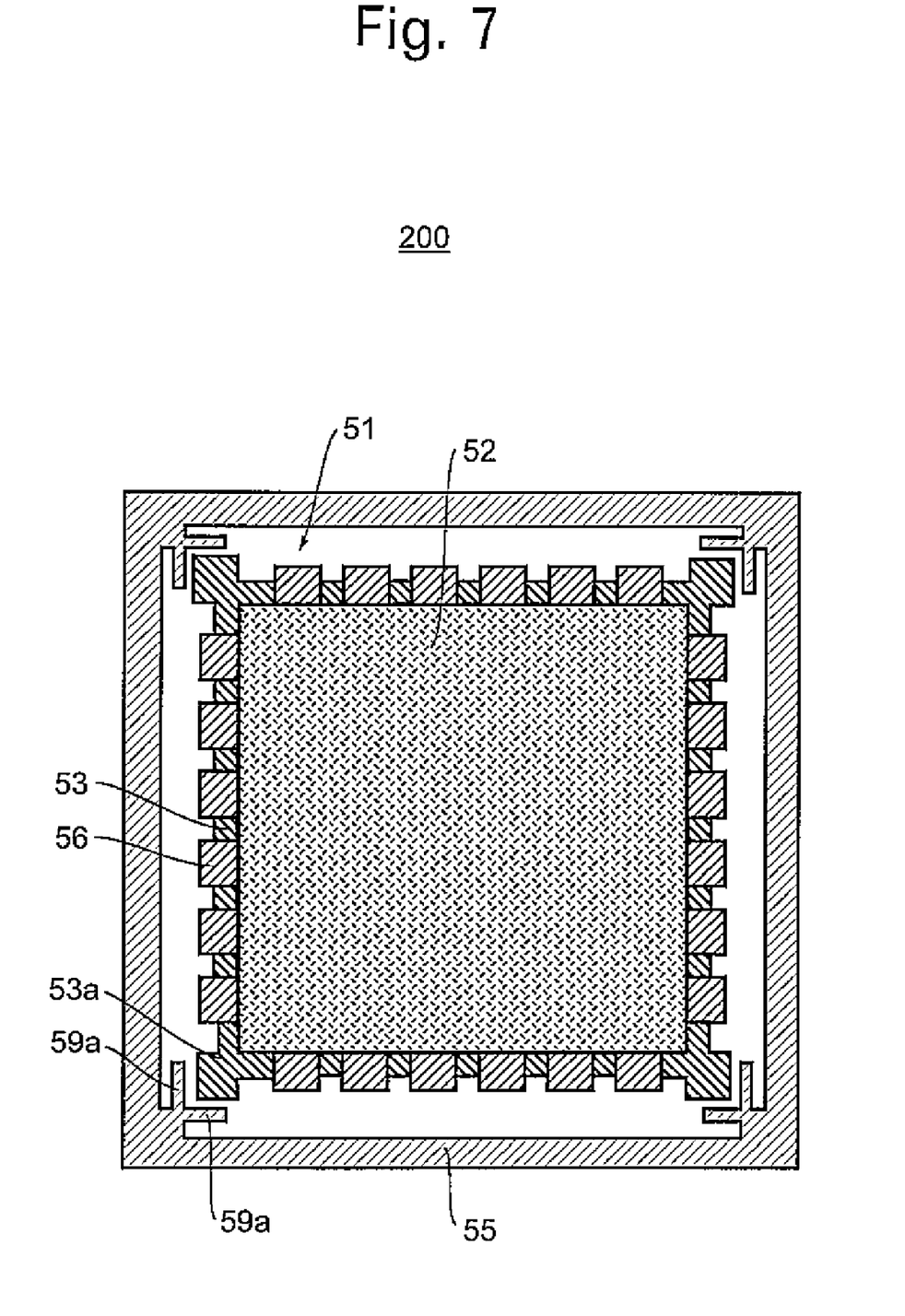
FIG. 7 is a horizontal sectional view showing another basic configuration of the detector panel shown in FIG. 4.

FIG. 7 is a horizontal sectional view showing one example of the internal configuration of the detector panel 200. As shown in FIG. 7, the case 55 has buffer members 59a at four corners of the inner peripheral surface. The buffer member 59a is composed of a pair of cantilevers that is flexible by the pressing force in the horizontal direction by the X-ray detector assembly 51 and has one end fixed to the case. An opening angle at the cantilever portion of a pair of cantilevers is 90 degrees. The buffer member 59a is integral with the case 55. The buffer member 59a is formed by integrally forming with the case 55.

Figure 8:
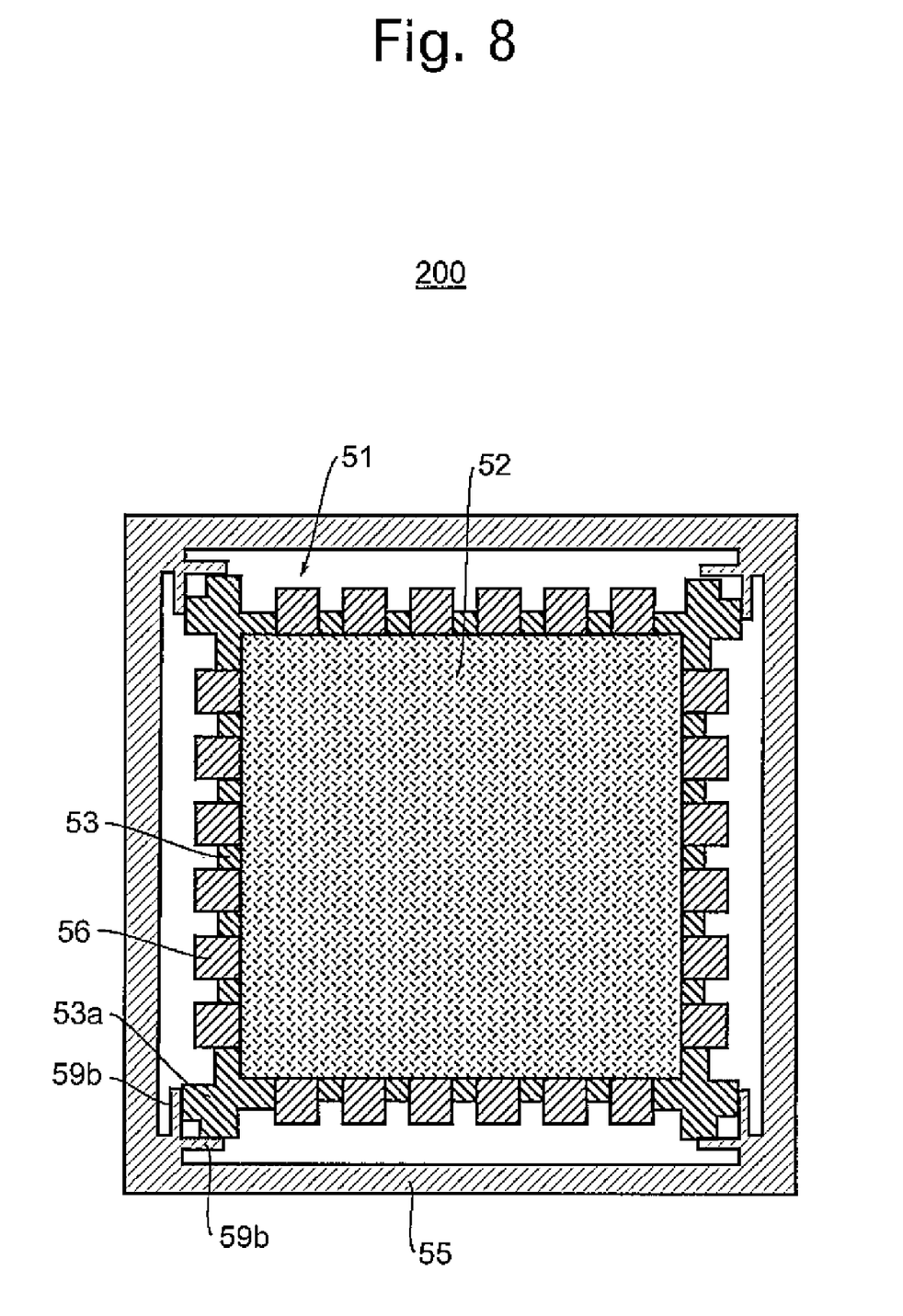
FIG. 8 is a horizontal sectional view showing another basic configuration of the detector panel shown in FIG. 4.

The support substrate 53 has projecting portions 53a at four corners so as to correspond to the buffer members 59a. Four projecting portions 53a oppose to the corresponding buffer members 59a with a space. Alternatively, the projecting portions 53a may oppose to the buffer members 59a as being in contact therewith as shown in FIG. 8.

According to the configuration of the case 55 and the support substrate 53, when the X-ray detector assembly 51 greatly displaces in the horizontal direction due to an extreme shock or vibration, the X-ray detector assembly 51 is elastically caught by the buffer members 59a, whereby the shock is eased.

Figure 9:
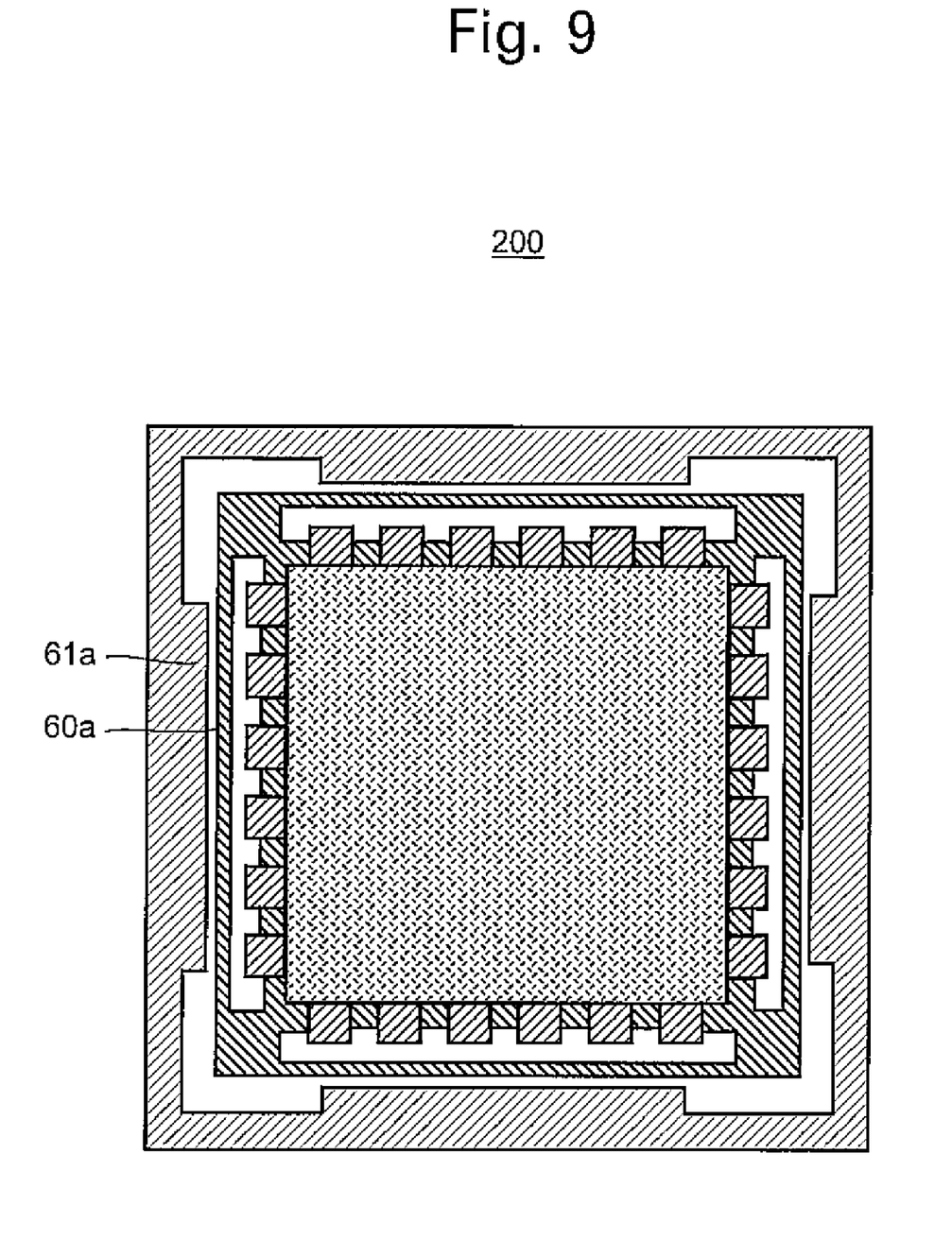
FIG. 9 is a horizontal sectional view showing another basic configuration of the detector panel shown in FIG. 4.

FIG. 9 is a horizontal sectional view showing another example of the internal configuration of the detector panel 200. As shown in FIG. 9, the support substrate 53 has buffer members 60a at its four sides. The buffer member 60a is composed of a fixed beam that is flexible by the pressing force in the horizontal direction by the X-ray detector assembly 51, wherein both ends thereof are fixed to the support member 53.

The buffer member 60a is integral with the support substrate 53. The buffer member 60a described above is formed by integrally forming with the support substrate 53.

Figure 10:
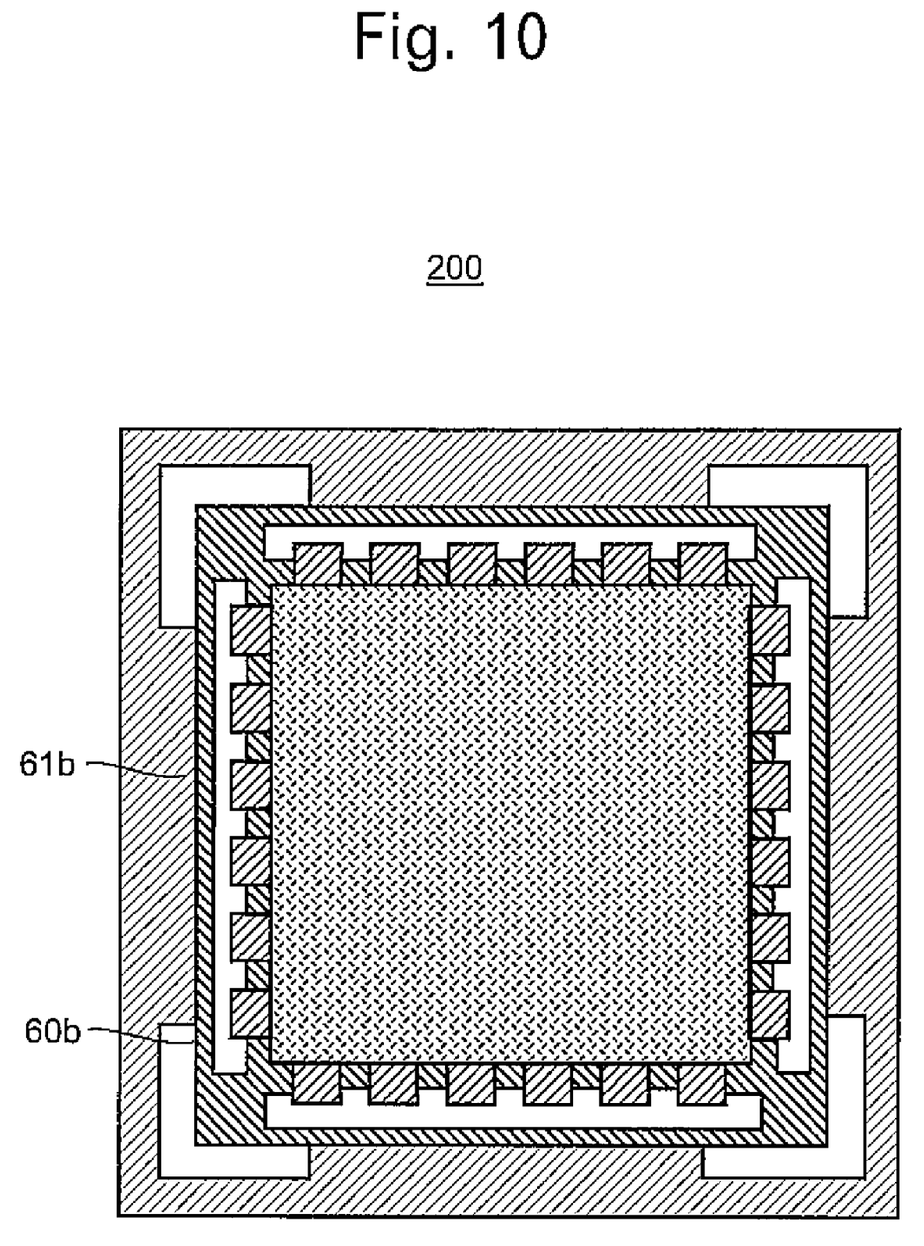
FIG. 10 is a horizontal sectional view showing another basic configuration of the detector panel shown in FIG. 4.

The case 55 has projecting portions 61a at the inner peripheral surface of four sides so as to correspond to the buffer members 60a. Four projecting portions 61a oppose to the corresponding buffer members 60a with a space. Alternatively, the projecting portions 61b may oppose to the buffer members 60b as being in contact therewith as shown in FIG. 10.

According to the configuration of the case 55 and the support substrate 53, when the X-ray detector assembly 51 greatly displaces in the horizontal direction due to an extreme shock or vibration, the X-ray detector assembly 51 is elastically caught by the buffer members 60a, whereby the shock is eased.

What is claimed is:

1. A portable detector panel comprising:
    an X-ray detector assembly comprising an X-ray detecting surface;
    a box-like case configured to house said X-ray detector assembly therein and comprising an X-ray transmissive upper part positioned opposite said X-ray detecting surface; and
    a spacer configured to support said X-ray detector assembly and positioned apart from an inner bottom wall of said case, said spacer arranged between said X-ray detector assembly and said inner bottom wall of said case, said spacer comprising a hard material, integrally formed with one of said X-ray detector assembly and said case, and having a flexible shape with respect to movement of said X-ray detector assembly in a direction substantially parallel to said X-ray detecting surface.

2. A portable detector panel according to claim 1, wherein the flexible shape of said spacer with respect to the movement of said X-ray detector assembly in the direction substantially parallel to said X-ray detecting surface is a cylindrical shape in which a first part thereof in a height direction, which is a direction vertical to said inner bottom wall of said case, is narrower than a second part.

3. A portable detector panel according to claim 1, wherein the flexible shape of said spacer with respect to the movement of said X-ray detector assembly in the direction substantially parallel to said X-ray detecting surface is a cylindrical shape in which at least a central part is hollow.

4. A portable detector panel according to claim 1, wherein said X-ray detector assembly further comprises:
    a support substrate;
    an X-ray detector supported on an upper surface of said support substrate;
    an electric circuit board supported on a lower surface of said support substrate; and
    a flexible circuit board configured to electrically connect said X-ray detector and said electric circuit board.

5. A portable detector panel according to claim 4, wherein said spacer is coupled to said support substrate of said X-ray detector assembly and to said inner bottom wall of said case.

6. A portable detector panel according to claim 1, wherein said spacer comprises a plurality of spacers, each provided at a corner of said X-ray detector assembly.

7. A portable detector panel according to claim 1, further comprising:
    a buffer member positioned between an inner side wall of said case and the X-ray detector assembly, said buffer member composed of a hard material, and having a flexible shape with respect to the movement of said X-ray detector assembly in the direction generally parallel to said X-ray detecting surface.

8. A portable detector panel according to claim 7, wherein said buffer member comprises a beam that is arranged on said inner side wall of said case and is flexible with respect to a pressing force imparted to said X-ray detector assembly in the direction generally parallel to said X-ray detecting surface.

9. A portable detector panel according to claim 7, wherein said buffer member comprises a beam that is arranged between said inner side wall of said case and said X-ray detector assembly and is flexible with respect to a pressing force imparted to said X-ray detector assembly in the direction generally parallel to said X-ray detecting surface.

10. An X-ray imaging apparatus comprising:
    a system console comprising an X-ray irradiator and a control circuit; and
    a portable detector panel configured to detect an X-ray generated from said X-ray irradiator, said detector panel comprising:
        an X-ray detector assembly comprising an X-ray detecting surface;
        a box-like case configured to house said X-ray detector assembly therein and comprising an X-ray transmissive upper part positioned opposite said X-ray detecting surface; and
        a spacer configured to support said X-ray detector assembly and positioned apart from an inner bottom wall of said case, said spacer arranged between said X-ray detector assembly and said inner bottom wall of said case, said spacer comprising a hard material, integrally formed with one of said X-ray detector assembly and said case, and having a flexible shape with respect to movement of said X-ray detector assembly in a direction substantially parallel to said X-ray detecting surface.

11. An X-ray imaging apparatus according to claim 10, wherein the flexible shape of said spacer with respect to the movement of said X-ray detector assembly in the direction substantially parallel to said X-ray detecting surface is a cylindrical shape in which a first part thereof in a height direction, which is a direction vertical to said inner bottom surface of said case, is narrower than a second part.

12. An X-ray imaging apparatus according to claim 10, wherein the flexible shape of said spacer with respect to the movement of said X-ray detector assembly in the direction substantially parallel to said X-ray detecting surface is a cylindrical shape in which at least a central part is hollow.

13. An X-ray imaging apparatus according to claim 10, wherein said X-ray detector assembly comprises:
    a support substrate;
    an X-ray detector supported on an upper surface of said support substrate;
    an electric circuit board supported on a lower surface of said support substrate; and
    a flexible circuit board configured to electrically connect said X-ray detector and said electric circuit board.

14. An X-ray imaging apparatus according to claim 13, wherein said spacer is coupled to said support substrate of said X-ray detector assembly and to said inner bottom wall of said case.

15. An X-ray imaging apparatus according to claim 10, wherein said spacer comprises a plurality of spacers, each spacer provided at a corner of said X-ray detector assembly.

16. An X-ray imaging apparatus according to claim 10, further comprising:
    a buffer member positioned between an inner side wall of said case and said X-ray detector assembly, said buffer member composed of a hard material, and having a flexible shape with respect to the movement of said X-ray detector assembly in the direction generally parallel to said X-ray detecting surface.

17. An X-ray imaging apparatus according to claim 16, wherein said buffer member comprises a beam that is arranged on said inner side wall of said case and is flexible with respect to a pressing force imparted on said X-ray detector assembly in the direction generally parallel to said X-ray detecting surface.

18. An X-ray imaging apparatus according to claim 16, wherein said buffer member comprises a beam that is arranged between said inner side wall of said case and said X-ray detector assembly and is flexible with respect to a pressing force imparted on said X-ray detector assembly in the direction generally parallel to said X-ray detecting surface.

19. A method of assembling a detector panel configured for use with an X-ray imaging apparatus, said method comprising:
providing an X-ray detector assembly that includes an X-ray detecting surface;
positioning the X-ray detector assembly within a case, the case including an X-ray transmissive upper part positioned opposite the X-ray detecting surface; and
positioning a spacer with respect to the X-ray detector assembly such that the spacer is positioned apart from an inner bottom wall of the case, the spacer arranged between the X-ray detector assembly and the inner bottom wall, the spacer comprising a hard material, integrally formed with one of the X-ray detector assembly and the case, and having a flexible shape with respect to movement of the X-ray detector assembly in a direction substantially parallel to the X-ray detecting surface.

20. A method according to claim 19, further comprising:
providing a support substrate within the X-ray detector assembly;
positioning an X-ray detector with respect to an upper surface of the support substrate;
positioning an electric circuit board with respect to a lower surface of the support substrate; and
coupling the X-ray detector and the electric circuit board using a flexible circuit board.

* * * * *